(12) United States Patent
Beruda et al.

(10) Patent No.: US 11,911,251 B2
(45) Date of Patent: Feb. 27, 2024

(54) ABSORBENT ARTICLE WITH HIGH TOUGHNESS ADHESIVE

(71) Applicant: The Procter & Gamble Company, Cincinnati, OH (US)

(72) Inventors: Holger Beruda, Schwalbach (DE); Torsten Lindner, Kronberg (DE); Matthias Morand, Sulzbach (DE); Thomas Tombuelt, Nettersheim (DE); Robert Haines Turner, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 430 days.

(21) Appl. No.: 17/151,795

(22) Filed: Jan. 19, 2021

(65) Prior Publication Data

US 2021/0228425 A1 Jul. 29, 2021

Related U.S. Application Data

(60) Provisional application No. 62/966,135, filed on Jan. 27, 2020.

(51) Int. Cl.
*A61F 13/539* (2006.01)
*A61F 13/49* (2006.01)
(Continued)

(52) U.S. Cl.
CPC ...... *A61F 13/539* (2013.01); *A61F 13/49011* (2013.01); *A61F 13/4963* (2013.01);
(Continued)

(58) Field of Classification Search
CPC .............. A61F 13/539; A61F 13/49011; A61F 13/4963; A61F 2013/53908;
(Continued)

(56) References Cited

U.S. PATENT DOCUMENTS

| 5,026,756 A | 6/1991 | Arendt |
| 5,723,546 A | 3/1998 | Sustic |

(Continued)

FOREIGN PATENT DOCUMENTS

| EP | 0571882 A3 | 7/1994 |
| WO | 2014093323 A1 | 6/2014 |

(Continued)

OTHER PUBLICATIONS

PCT Search Report and Written Opinion for PCT/US2021/013851 dated May 17, 2021.

*Primary Examiner* — Susan S Su
(74) *Attorney, Agent, or Firm* — Amanda Herman Berghauer; Daniel Albrecht

(57) ABSTRACT

An absorbent article (20, 20') comprising a topsheet (58), a backsheet (42,60), and an absorbent core (62), and at least one nonwoven-nonwoven adhesive bond other than a core stabilization bond, wherein the adhesive of the adhesive bond has a Toughness of at least 11 MJ/m³, a Yield Stress of at least 0.7 MPa. The adhesive may further have a storage modulus G' of at least 7.5 MPa. These are as measured at 37° C. according to the methods described herein. The adhesive comprises at least 5% by weight of the adhesive of a tackifier.

20 Claims, 6 Drawing Sheets

(51) Int. Cl.
*A61F 13/496* (2006.01)
*A61L 15/26* (2006.01)
*A61L 15/58* (2006.01)

(52) U.S. Cl.
CPC ............... *A61L 15/26* (2013.01); *A61L 15/58* (2013.01); *A61F 2013/53908* (2013.01)

(58) Field of Classification Search
CPC .. A61F 2013/15292; A61F 2013/15569; A61F 2013/539; A61L 15/26; A61L 15/58
See application file for complete search history.

(56) References Cited

U.S. PATENT DOCUMENTS

| | | | |
|---|---|---|---|
| 8,653,169 B2 † | 2/2014 | Jiang | |
| 10,370,567 B2 | 8/2019 | Moriguchi | |
| 2011/0021103 A1* | 1/2011 | Alper | B32B 5/26 524/505 |
| 2012/0184933 A1 | 7/2012 | Floeter et al. | |
| 2014/0358100 A1 | 12/2014 | Remmers | |
| 2016/0053149 A1 | 2/2016 | Herrlich | |
| 2016/0256592 A1* | 9/2016 | Lindner | A61L 15/24 |
| 2016/0270987 A1* | 9/2016 | Stiehl | A61F 13/539 |
| 2017/0290945 A1 | 10/2017 | Hanson et al. | |
| 2018/0037778 A1 | 2/2018 | Briseno et al. | |
| 2018/0168891 A1* | 6/2018 | Wise | A61F 13/4902 |
| 2019/0322900 A1 † | 10/2019 | Turner | |

FOREIGN PATENT DOCUMENTS

| | | |
|---|---|---|
| WO | 2015031225 A1 | 3/2015 |
| WO | 2015183669 A1 | 12/2015 |
| WO | 2016060922 A1 | 4/2016 |
| WO | 2016133712 A1 | 8/2016 |
| WO | 2016149251 A1 | 9/2016 |
| WO | 2016149252 A1 | 9/2016 |
| WO | 2017106153 A3 | 8/2017 |
| WO | 2017173894 A1 | 10/2017 |

\* cited by examiner
† cited by third party

ABSORBENT ARTICLE WITH HIGH TOUGHNESS ADHESIVE

CROSS REFERENCE TO RELATED APPLICATIONS

This application claims the benefit, under 35 U.S.C. § 119(e), of U.S. Provisional Patent Application Ser. No. 62/966,135, filed on Jan. 27, 2020, the entire disclosure of which is incorporated by reference herein.

FIELD

The present disclosure relates to disposable absorbent articles, in particular pant diapers and taped diapers, comprising at least a nonwoven-nonwoven adhesive bond. The adhesive provides nonwoven-nonwoven bonds that are particularly resistant to peel creep forces.

BACKGROUND

Disposable personal hygiene absorbent articles such as baby diapers, training pants and adult incontinence articles have become irreplaceable for receiving and retaining bodily discharges such as urine or feces from incontinent persons. These absorbent articles comprise a liquid pervious topsheet that faces internally towards the wearer's body, a liquid impervious backsheet that faces externally and an absorbent layer interposed between the topsheet and the backsheet. Other components are typically present in absorbent articles, such as fluid acquisition and/or distribution layers, inner and outer barrier leg cuffs, elastics, core wraps, etc.

Typical absorbent articles include pant diapers which have side seams and are pulled up on the legs of the wearer similarly to an underwear. A particular type of pant design currently marketed is sometimes called the "balloon" pant. The balloon pant design usually includes a central absorbent chassis and an elastic belt. The elastic belt is usually relatively wide (in the longitudinal direction) and elastically stretchable in the lateral direction. It entirely encircles the wearer's waist, and thereby covers a relatively large amount of the wearer's skin and makes up a relatively large portion of the visible outside surfaces of the pant. The central chassis portion is typically joined to the inside of the belt in the front, wraps under the wearer's lower torso between the legs, and is joined to the inside of the belt in the rear. As such, balloon pants are a compilation of separate article components.

Other common absorbent articles include taped diapers, which comprise two back ears with tapes that can be fastened to a landing zone disposed on the front of the diaper to form the waist and leg openings. Typically, the tapes have at their extremities a plurality of small hooks that can be releasably engaged with a suitable receiving surface on a discrete piece of material called landing zone which is disposed on the front of the diaper (hook and loop type fastener). The landing zone is also a component of the diaper that needs to be securely attached to the backsheet of the diaper.

The components of the absorbent articles must be directly or indirectly bonded to each other. While thermo-bonding or ultrasonic bonding is increasingly used in the industry, these non-adhesive bonding methods require higher basis weight material and cannot be used for continuous bonding over large area. Thus, adhesive bonding of a variety of substrates will remain in usage for absorbent articles in the future.

Hotmelt adhesives are typically used to make adhesive bonds on absorbent articles. Hotmelt adhesives are thermoplastic compositions solid at room temperature. When heated, they are converted into the liquid or molten state, i.e. the hotmelt adhesive is open, and may be applied to a substrate. When a second substrate is applied with some pressure to the hotmelt adhesive before it has re-cooled to the solid state, an adhesive bond between the two substrates may be formed. The hotmelt adhesive has an open time optimized for the intended use and effects permanent adhesive bonding of the adherends. Conventional hotmelt adhesives typically contain a cohesive base polymer, an adhesive tackifier and optionally waxes, plasticizers (oils) and further additives.

Hotmelt adhesives can be applied by contact applicators such as slot glue applicator, or non-contact applicators such as spray or spiral applicators, as is known in the art. Typical hotmelt adhesives and their function are described in U.S. Pat. No. 5,026,756 (Arendt) for example.

WO 2017/106153 A2 (Turner, P&G) discloses a pant article wherein adhesive bonds are formed by an adhesive which is substantially tackifier free. The tackifier free adhesive comprises (i) an amorphous polyolefin composition and an heterophase polyolefin composition comprising amorphous character and crystalline character.

WO 2016/149252 A1 (Stiehl et al., P&G) discloses an absorbent core comprising a fiberized net structure formed by a composition having a storage modulus (G') at 21° C. of greater than about $1.2 \times 10^6$ Pa.

U.S. Pat. No. 10,350,325 (Remmers et al., H. B. Fuller) discloses an adhesive composition for absorbent articles including a first propylene-based polymer that has a Mw of no greater than about 75,000, and a second polymer that is also propylene-based and has a Mw of at least about 100,000. The adhesive composition is used for at least two applications in the disposable absorbent article and is delivered via a molten bulk tank. This document discloses using the hotmelt adhesive formulations for bonding the backsheet film to a nonwoven or elastic attachment, and for core stabilization, but not for other nonwoven-nonwoven bonds.

Some bonds in diapers need to withstand demanding requirements related to "peel creep", i.e. exposure of a sustained peeling force over an extended period of time at a temperature close to body temperature. For example, the elasticized belts in a pant diaper are under continuous tension during use. Another example is the landing zone material that is attached to the front side of taped diapers and on which the back ear tapes are releasably fastened during use. The peel creep resistance of a bond can be measured via static hang tests. It was found that a load applied in the "Peel" configuration is more damaging to bonds than a load applied in the "Shear" configuration. As peel creep is the most damaging load case for bonds made with viscoplastic adhesives such as polyolefin-based adhesives, the static hang test in the peel configuration ("peel hang test") is applied as the most conservative test for bonds with viscoplastic conditions. This is particularly useful if the actual in-use load for a bond is not known, or if a number of different loads can occur simultaneously or subsequently (e.g. both shear and peel forces occurring due to the baby's movement on wearing the diaper, or the baby trying to open a bond with his hands by slowly peeling the substrates). If a bond has good peel creep resistance, it will typically also survive all other typical use conditions and can be used for other bonds in the diapers.

It was also found that the required properties of adhesives for NW-NW bonds are very different than for NW-Film bonds. As such there is a need for adhesives that are particularly useful for NW-NW bonds that require peel creep resistance.

SUMMARY OF THE INVENTION

Figure 1:
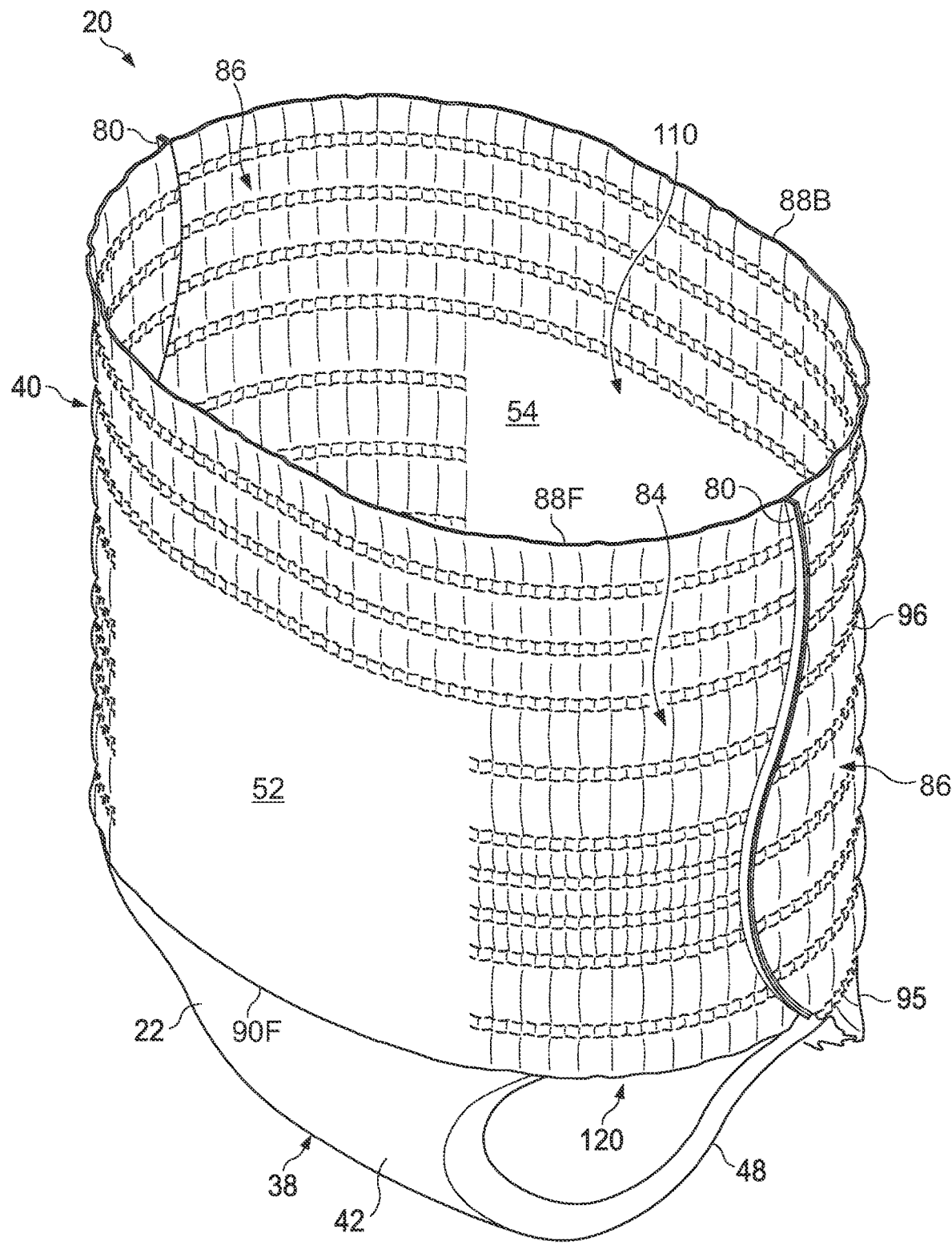
FIG. 1 is a perspective view of one example of a belted pant diaper.

In a first aspect, the invention is for an absorbent article comprising a topsheet, a backsheet, and an absorbent core, and at least one nonwoven-nonwoven adhesive bond, other than a core stabilization bond, using an adhesive having selected properties. The absorbent core is typically present for most absorbent articles but can be optional for swim pants for example. The present invention may be used to provide adhesive bonding between two nonwovens in pant diapers as well as taped diapers. At least one of the adhesive bonds may be a bond that is submitted to creep peel force during usage. For pant diapers such high requirement adhesive bonds include the belt panel bond, the chassis-to-belt bond, the waist fold bond and the front belt to back belt bonds that form the side seams of the pant diaper. For taped diapers such adhesive bonds include the landing zone to backsheet outer cover bond. The adhesive of the invention may also be used for other bond application having less requirements, for example any adhesive bonding between the topsheet and an acquisition layer, and/or between an acquisition layer and the core wrap of absorbent core, and/or the topsheet and the core wrap of the absorbent core.

It was found that the adhesives of the invention having a Toughness of at least 11 MJ/m$^3$, preferably at least 22 MJ/m$^3$ and a Yield Stress of at least 0.7 MPa, preferably at least 1.0 MPa, are particular efficient for nonwoven to nonwoven (NW-NW) adhesive bond, in particular for such bonds submitted to peel creep during usage of the diaper, and more generally to any nonwoven-nonwoven bonds. The adhesives of the invention comprises at least 5% by weight of the adhesive of a tackifier. The adhesive may also have a storage modulus (G') of at least 3 MPa, preferably at least 7.5 MPa. These properties are as measured at 37° C. according to the methods described herein.

Accordingly, the invention allows cost saving by decreasing the amount of adhesive conventionally used and/or allows improved performance at same amount usage over conventional adhesives.

Various non-limiting embodiments of the present disclosure will now be described to provide an overall understanding of the principles of the structure, function, manufacture, and use of the absorbent articles disclosed herein. One or more examples of these non-limiting embodiments are illustrated in the accompanying drawings. Those of ordinary skill in the art will understand that the absorbent articles described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

DETAILED DESCRIPTION

The following term explanations may be useful in understanding the present disclosure.

"Absorbent article" or "personal hygiene absorbent article", as used herein, refers to devices that are placed against or in proximity to the body of the wearer to absorb and contain the various exudates discharged from the body. Absorbent articles of the invention include taped diapers and pant diapers. Their size may be adapted for babies, young children or for adults suffering incontinence. While the absorbent articles are disposable and typically discarded after usage, they are preferably recycled or otherwise disposed of in an environmentally compatible manner.

The terms "elastic," "elastomer," and "elastomeric" refer to a material which generally is able to extend to a strain of at least 50% without breaking or rupturing, and is able to recover substantially to its original dimensions after the deforming force has been removed.

"Longitudinal" refers to the direction along the axis (L1, L2 in the Figures) extending from the midpoint of the front waist edge to the midpoint of the rear waist edge of the absorbent article, and that bisects the absorbent article into a left half and right half. "Transversal" refers to the direction perpendicular to the longitudinal line (T1, T2 in the Figures).

The term "pant" or "pant diaper" refers to absorbent articles which have a defined waist opening and a pair of leg openings and which are placed on the body of the wearer by inserting the legs into the leg openings and pulling the article up over the waist. Pant diapers comprise a central chassis with topsheet, backsheet and absorbent core combined with a waist belt having a front belt and back belt. While the terms "pant" or "pant diapers" are used herein, pants are also commonly referred to as "closed diapers," "prefastened diapers," "pull-on diapers," "training pants," and "diaper-pants". Such a pant diaper is shown in FIG. 1 for example.

Figure 5:
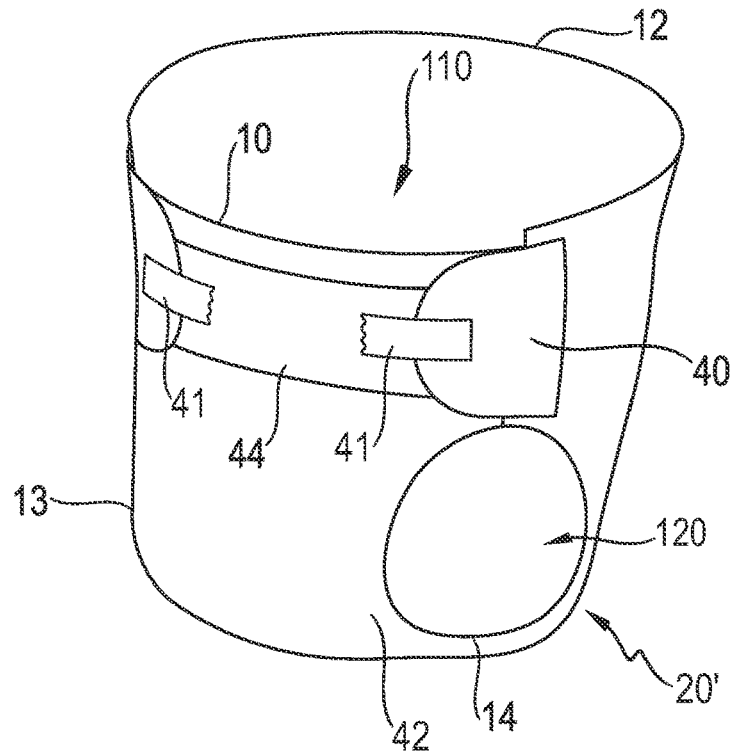
FIG. 5 shows a perspective view of an exemplary taped diaper in a closed configuration as it would be when worn by a wearer.
Figure 6:
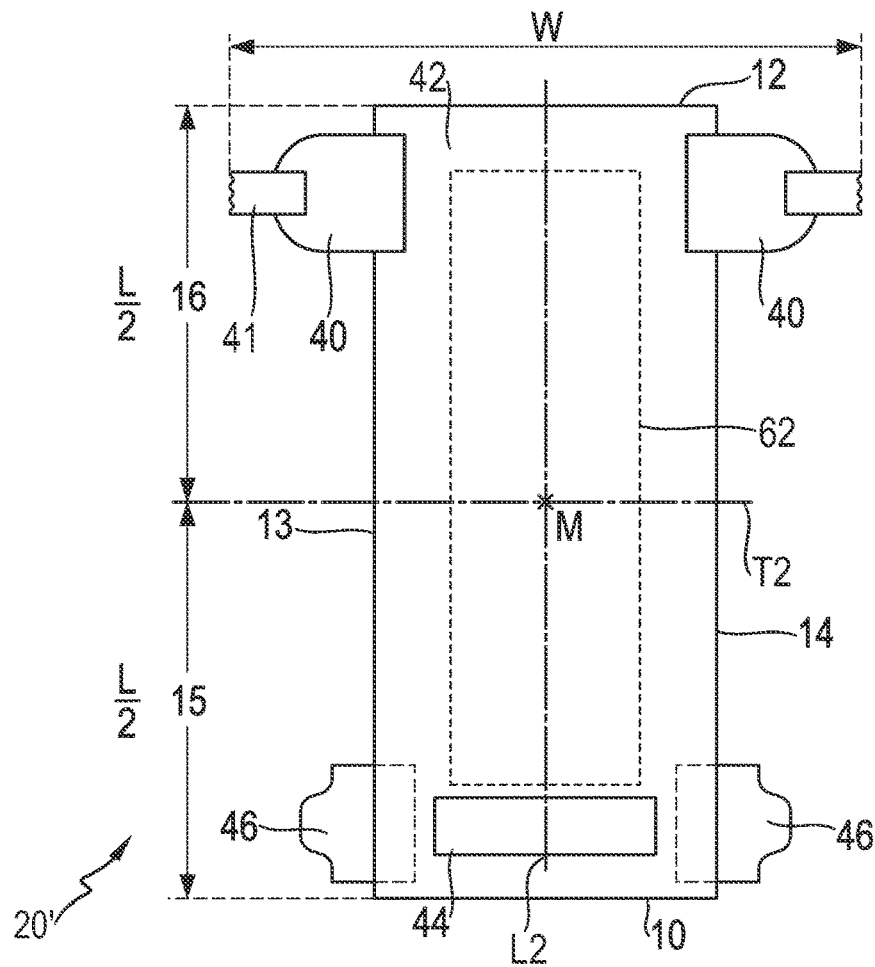
FIG. 6 shows the external-facing side of the diaper of FIG. 5 flattened out with the tapes open.
Figure 7:
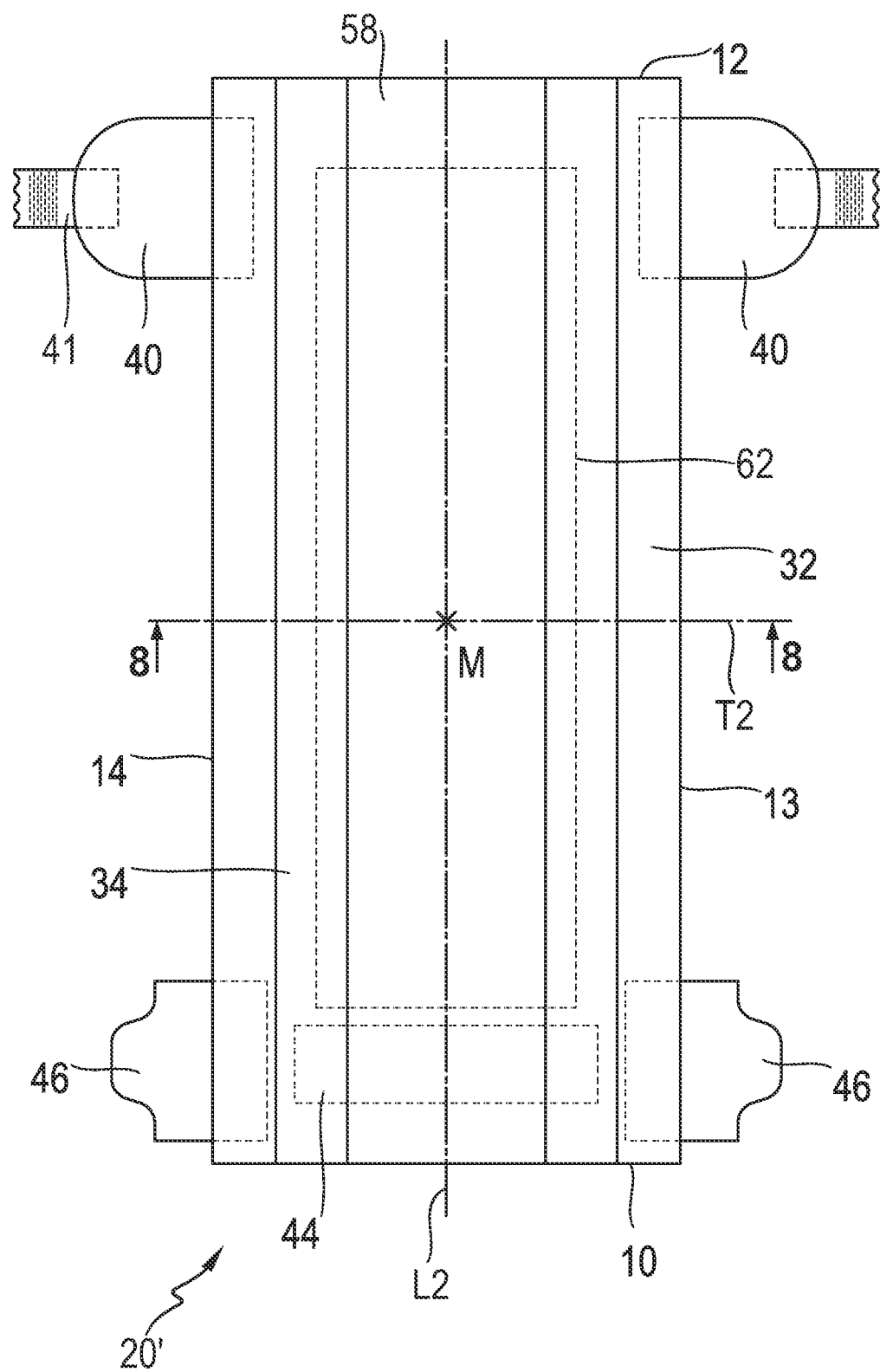
FIG. 7 shows the internal-facing side of the diaper of FIG. 5 flattened out with the tapes open.

The term "Taped diaper" refers herein to absorbent articles that comprises tapes, typically in the back half of the product, that can be refastenably attached to a landing zone (typically on the front of the diaper) to create the waist and legs openings. Such a taped diaper is shown in FIGS. 5-7 for example.

As used herein, the terms "nonwoven", nonwoven layer" or "nonwoven web" are used interchangeably to mean an engineered fibrous assembly, primarily planar, which has been given a designed level of structural integrity by physical and/or chemical means, excluding weaving, knitting or papermaking (ISO 9092:2019 definition). The directionally or randomly orientated fibers, are bonded by friction, and/or cohesion and/or adhesion. The fibers may be of natural or synthetic origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter (g/m$^2$ or gsm).

"Comprise," "comprising," and "comprises", as used herein, are open ended terms, each specifies the presence of what follows, e.g., a component, but does not preclude the presence of other features, e.g., elements, steps, components known in the art, or disclosed herein.

"Consisting essentially of", as used herein, limits the scope of subject matter, such as that in a claim, to the specified materials or steps and those that do not materially affect the basic and novel characteristics of the subject matter. The term "Consisting of" further limits the scope to the specified elements, steps, or components.

"Substantially", as used herein, means generally the same or uniform but allowing for or having minor fluctuations from a defined property, definition, etc. For example, small measurable or immeasurable fluctuations in a measured property described herein, such as viscosity, melting point, etc. may result from human error or methodology precision. Other fluctuations are caused by inherent variations in the manufacturing process, thermal history of a formulation, and the like. The compositions of the present invention, nonetheless, would be said to be substantially having the property as reported.

Pant Diaper 20

The absorbent articles of the invention may be pant diapers. FIGS. 1-4 illustrate in a non-limiting manner such a pant diaper 20 comprising of a central chassis 38 and a waist belt 40. The pant diaper construction will be briefly discussed therein, acknowledging that such construction is known in the art. A more detailed description of a typical pant construction is for example disclosed in WO 2017/173894 (P&G). The components of the chassis including topsheet, backsheet, absorbent core, inner and outer cuffs, can be made of similar components as found in taped diapers 20', and are discussed further below.

Figure 2:
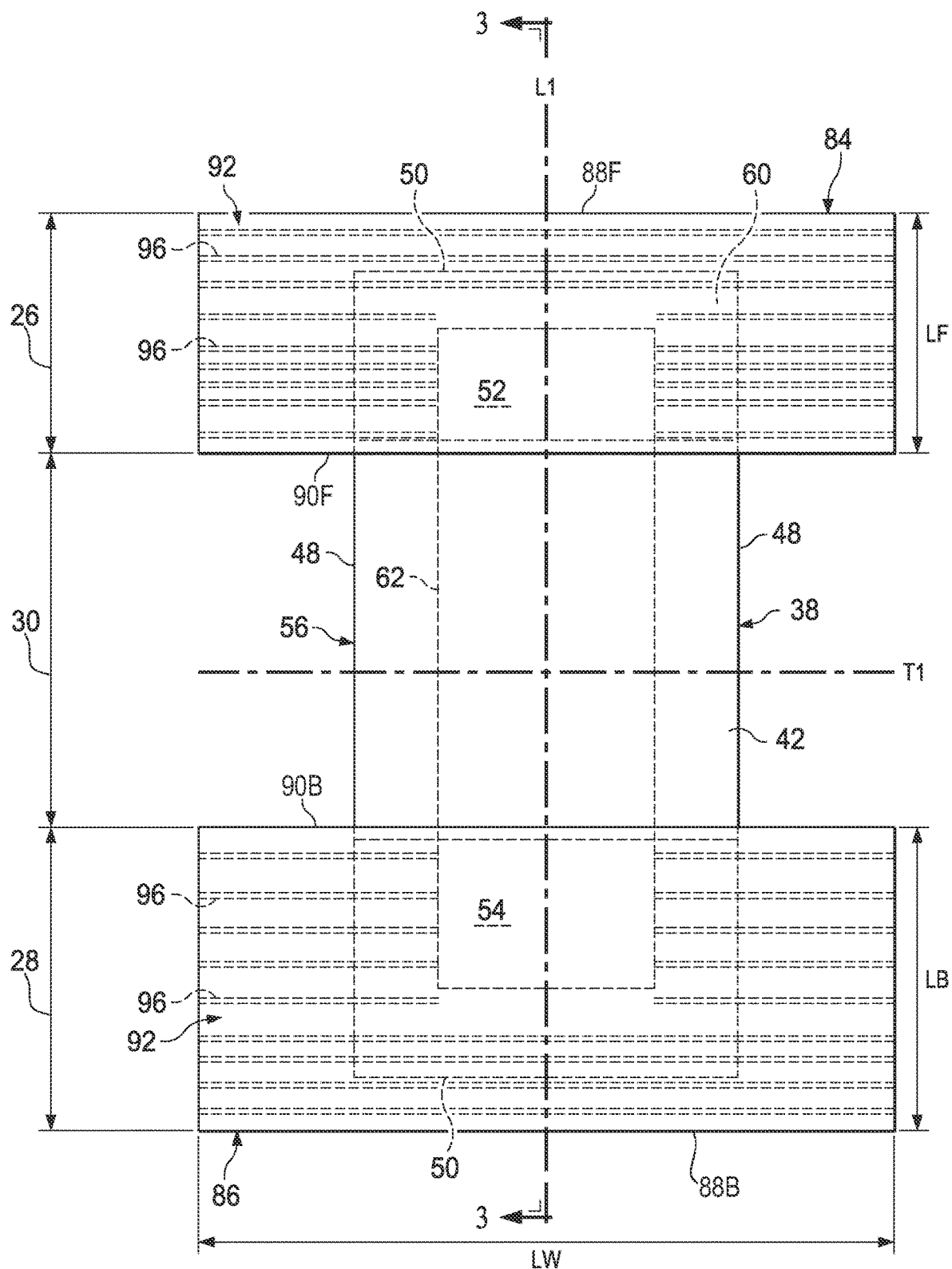
FIG. 2 is a schematic plan view of a belted pant diaper precursor structure, prior to joining of the front and rear sections of the belt.

FIG. 1 is a perspective view of an embodiment of a pant diaper 20. FIG. 2 is a schematic plan view of the garment-facing surface of the pant diaper of FIG. 1 without the side seams 80 and in a flat uncontracted state. As shown in FIG. 2, the pant diaper 20 has a longitudinal axis L1 which notionally divides the pant in a left half and a right half, and a transverse axis T1 perpendicular to L1 which divides the pant in a front half and back half of equal length.

The pant diaper 20 has a topsheet 58 on its wearer-facing surface. The pant diaper further has a backsheet laminate comprising a fluid-impermeable film 60 and a nonwoven outer cover layer 42 on its garment-facing surface. The pant diaper can be further divided in a front region 26, a back region 28, and a crotch region 30 between the front region 26 and the back region 28. The front region 26 is defined by the front belt 84 and the back region 28 by the back belt 86.

The front belt 84 and the back belt 86 jointly form a ring-like elastic belt 40 (hereinafter referred to as "waist belt") extending transversely. The front belt 84 and the back belt 86 are joined by seams 80 at their transversal side edges to form, with the central chassis 38, a waist opening 110 and the two leg openings 120. One or both of the belt portions 84, 86 may be disposed on the garment-facing surface of the central chassis 38 or alternatively on the body-facing surface of the central chassis 38.

The pant diaper 20 comprises a central chassis 38 disposed in the crotch region 30 and at least partially longitudinally extending to the front region 26 and back region 28 of the pant diaper. The central chassis 38 further comprises an absorbent core 62 for absorbing and containing body exudates, a fluid impermeable backsheet film 60 at least partially laminated to a nonwoven outer cover 42 on the article's garment-facing side, and a liquid permeable topsheet 58.

The central chassis 38 has a generally rectangular shape, with left and right longitudinally extending side edges 48 (hereinafter may be referred to as "side edge") and a front and back transversely extending end edges 50 (hereinafter may be referred to as "end edges"). The front and back belts 84, 86 typically overlap at least a portion of the central chassis 38.

The front waist panel 52 is the portion of the central chassis 38 overlapping the front belt 84 of the pant diaper 20, and the back waist panel 54 is the portion of the central chassis positioned overlapping the back belt 96 in the back region 28. The crotch panel 56 is the portion of the central chassis 38 disposed in the crotch region 30, and thus between the front waist panel 52 and back waist panel 54. The front belt 84 and back belt 86 are typically joined to the chassis 38 in the region of the front waist panel 52 and the back waist panel 54 respectively by an adhesive 72 forming a chassis-to-belt bond in these areas, which may be an adhesive according to the invention. In the drawings, the bonds and the adhesives forming the bonds are shown by the same reference number.

The waist belt 40 formed by the front belt 84 and back belt 86 acts to dynamically create fitment forces and to distribute the forces dynamically generated during wear. Herein, the term "proximal" is used to indicate the position of a "proximal" portion being closer relative to the transverse centerline T1 of the article. Therefore, the proximal edge 90 of the belt 40 is located closer than the distal edge 88 of the belt relative to the transverse centerline T1. The front and back belts 84, 86 may be joined with each other only at the seams 80 to form a pant diaper having a waist opening 110 and two leg openings 120. Each leg opening may be provided with elasticity around the perimeter of the leg opening by the combination of elasticity from the front belt 84, the back belt 86, and any elastics cuffs (not represented in FIGS. 1-5) from the central chassis 38.

The front belt portion 84 and the back belt portion 86 may be continuous or discontinuous with one another in the crotch region 30. When the front and back belts 84, 86 are discontinuous, there is no material that covers the entirety of either the wearer-facing surface or garment-facing surface of the article, as illustrated in FIG. 2. In other words, the waist belt does not extend into the crotch panel 56 of the central chassis 38.

The front belt 84 and back belt 86 each comprises an inner belt 94 and an outer belt 92. The inner belt 94 and outer belt 92 are typically nonwovens. The front and back belts 84, 86 may be provided in low caliper nonwoven material for sake of breathability and softness of the belt 40. The belt may comprise an inner hydrophobic, non-stretchable nonwoven material 94 and an outer hydrophobic, non-stretchable nonwoven material 92. The elastic strands 96 may comprise one or more elastic strands, elastomeric films, elastomeric ribbons, elastomeric nonwovens, elastomeric filaments, elastomeric adhesives, elastomeric foams, scrims or combinations thereof. Each of the front belt 84 and back belt 86 may be made as a laminate having a plurality of elastic strands 96 sandwiched between the inner belt 94 and outer belt 92 to impart elasticity in the front and back regions 26, 28. In one embodiment, the elastic strands 96 extend in a transverse direction to provide a ring like elastic belt 40 when the front belt 84 and the back belt 86 are joined. At least some of the elastic strands 96 extend in the transverse direction substantially parallel to each other. All of the elastic strands 96 may extend in the transverse direction substantially parallel to each other. Such an article may be economically made.

The front belt 84 and the back belt 86 may be made of the same or different materials. The elastic strands 96 disposition may also still be differentiated in the front and back belt, e.g. using different denier, interval, and force for the strands in the front and back belts, as well as in different longitudinal positions of the belt. The front and/or back belt 84, 86 may be treated such that certain of the area overlapping the front and/or back waist panel of the central chassis 38 are removed of elasticity. Removal of elasticity from the area where an artwork is displayed may help the visibility of the artwork.

The effective transversal width LW of the back belt 86 in the uncontracted condition may be the same as the transversal width of the front belt 84 of the same condition. By "effective transversal width", what is meant is the width available for forming the wearer-facing surface of the article. Each of the proximal edges 90 and the distal edges 88 of the front belt 84 and the back belt 86 may be substantially parallel, as in FIG. 2.

The longitudinal length LB of the back belt 86 between the back distal edge 88B and the back proximal edge 90B along its entire width LW of the back belt 86 may be approximately the same as the longitudinal length LF of the front belt 84 between the front distal edge 88 and the front proximal edge 90. In such embodiment, the seams 80 close the front and back belt 84, 86 side edges of the same length for forming the article. Such an article may be economically made.

The back belt 86 may have a greater longitudinal length LB between the back distal edge 88B and the back proximal edge 90B along its entire width LW than the longitudinal length LF of the front belt 84 between the front distal edge 88F and the front proximal edge 90F. In such embodiment, when the pant diaper is assembled to form the waist opening 110 and the leg openings 120, the pant diaper 20 is folded along the transverse centerline T1 such that the front distal edge 88F is aligned with the back distal edge 88B. The front side edges are also aligned with the back side edge. Then the front belt 84 and the back belt 86 are joined at their side edges to form a pair of seams 80. The front and back proximal edges 90, however, may also not be aligned to one another. The back proximal edge 90B may be disposed longitudinally closer to the transverse center line T1 than the front proximal edge 90F such that the back belt 86 extends toward the crotch panel 56 of the central chassis 38 beyond the front proximal edge 90F. The back proximal side edge 90B of the back belt 86 may not be joined to anywhere and thus free from attachment. In this way, the proximal portion of the back belt 86 provides a buttock cover 95 as in FIG. 1.

Whether or not the longitudinal length LB of the back belt 86 and the longitudinal length LF of the front belt 84 are the same, the entirety of the longitudinal length LF of the belt side edge of the front belt 84 may be seamed with the belt side edge of the back belt 86 to define a seam length LS. When the front belt 84 has straight distal edges 88F and proximal edges 90 that are substantially parallel of each other, then the longitudinal length LF of the front belt 84 is equal to the seam length LS.

Figure 3:
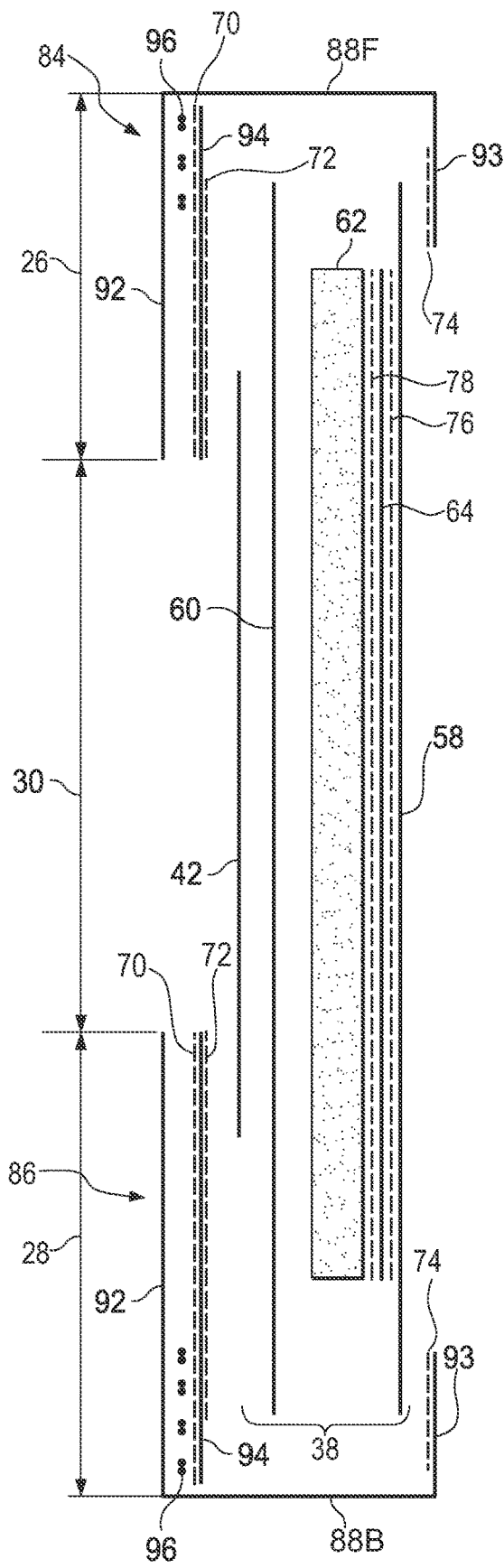
FIG. 3 is a schematic cross section view of a first embodiment taken along line 3-3 in FIG. 2.
Figure 4:
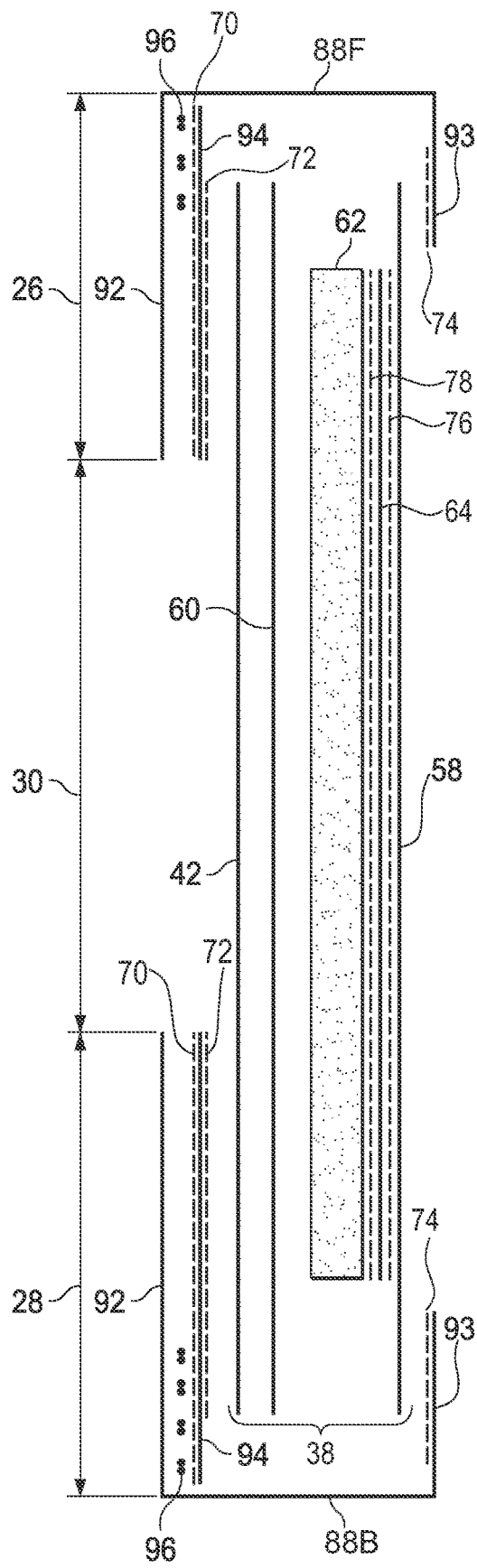
FIG. 4 is a schematic cross section view of a second embodiment along line 3-3 in FIG. 2.

Referring to FIGS. 3 and 4, the outer belt 92 of the front belt 84 and/or back belt 86 may be longer than the inner belt 94 in the longitudinal direction towards the respective distal edge 88, and an end flap 93 of the outer belt 92 may be folded over the distal end of the inner belt 94 at the waist opening to form an outer belt fold over 93 at the front and/or back belt.

The central chassis 38 comprises a backsheet. Backsheet are typically a laminate comprising a liquid impermeable backsheet film 60 attached to a nonwoven outer cover layer 42. The nonwoven outer cover forms the garment-facing side of the backsheet. The outer core layer 42 is typically attached by spiral gluing to the backsheet film 60, with both layers designated as the backsheet of the article. The outer cover layer 42 thus forms a portion the garment-facing surface 22 of the pant diaper 20, and covers at least the crotch panel 56 of the central chassis 38. The outer cover layer 42 may extend into and covers part of one or both of the front waist panel 52 and the back waist panel 54 of the central chassis 38.

Pant Diaper Adhesive Bonds

The front and back belts 84, 86 are typically joined respectively to the front and back waist panels 52, 54 of the central chassis 38 through the outer cover layer 42. As shown in FIGS. 3-4, the outer cover layer 42 is disposed between the front and back belt 84, 86 and the liquid impervious backsheet 60 of the central chassis 38. The outer cover layer 42 may be coterminous in the longitudinal direction with the backsheet 60 at the front panel 52 and/or back panel 54, as shown in FIG. 4. The inner belt 94 is attached to the outer cover 42 of the backsheet 38 in this area by the chassis-to-belt bond 72.

The outer cover layer 42 may also extend only partially in the longitudinal direction of the front waist panel 52 and/or the back waist panel 54 to leave the distal parts of the front waist panel 52 and/or the back waist panel 54 free of the outer cover layer 42, as illustrated in FIG. 3. Namely, the longitudinal length of the outer cover layer 42 may be longer than the longitudinal length of the crotch region 30 but shorter than the longitudinal length of the backsheet film 60. By such configuration, the distal parts of the front waist panel 52 and/or the back waist panel 54 are devoid of the outer cover layer 42, providing better breathability to the overall article. Furthermore, printed graphic on the portion of the backsheet film 60 not covered by the nonwoven outer cover 42 may be thus more visible on the garment-facing side of the pant diaper, as explained in more details in WO 2017/173894. However, even in this case a portion of the inner belt 94 is still attached to the nonwoven outer cover 42 of the backsheet in this area by the chassis-to-belt bond 72, with the backsheet film 60 attached to the rest of the inner belt 94. The adhesive 72 is typically applied first to the inner belt 94 before forming the chassis-to-belt bond.

While the adhesive of the invention may be used in a variety of bonds, it was found that certain pant diaper bonds can especially benefits from the inventive adhesive. These bonds are illustrated in FIGS. 3-4 and include the belt panel bond 70 which bonds the inner belt 94 to the outer belt 92, the chassis-to-belt bond 72 between the inner belt 94 and the chassis 38 (in particular to the nonwoven outer cover 42 of the chassis 38 as shown in FIG. 4 and optionally both the outer cover nonwoven 42 and the backsheet film 60 as shown in FIG. 3), the waist fold bond 74 which bonds the belt fold-over 93 to the chassis 38 (in particular the part of the chassis formed by the topsheet 58 as shown in FIGS. 3-4), and the side seam bonds 80 that bond the side edges of the front belt 84 to the side edges of the back belt 86 of the pant diaper.

Except for the side seams 80, these adhesive bonds are represented by the dotted lines showing the adhesive position in the FIGS. 3-4. The substrate closest to the dotted lines in the Figures represent the substrate on which the adhesive is typically applied first, before the other substrate is adhered thereto. For the belt panel bond 70, which bonds the inner belt 94 to the outer belt 92, the adhesive may thus be applied to the inner belt 94 before forming the belt laminate with the outer belt 92 and the elastic strands 96. For the chassis-to-belt bond 72 between the inner belt 94 and the part of chassis 38 formed by the backsheet laminate 48-60, the adhesive may be thus first applied to the inner belt 72. For the waist fold bond 74, which bonds the belt fold-over 93 to the chassis 38 (i.e. typically that part of the chassis formed by the topsheet 58), the adhesive 74 may be applied to the folded over portions 93 of the front and back belts 84,86. For the front belt 84 to back belt 86 bond that forms the side seams 80 of the pant diaper 20, there is no preference on which substrate the adhesive is applied first.

At least one, or two or more of the above mentioned adhesive bonds are preferably formed by the adhesive having the claimed properties, as these nonwoven-nonwoven bonds are submitted to creep peel forces during use of the diaper pants. In addition, other nonwoven to nonwoven bonds may benefit from using the adhesive claimed, in particular the adhesive may also be used to bond a nonwoven acquisition layer 64 to the topsheet 58 (topsheet to acquisition layer bond 76) and/or an acquisition layer 64 to an absorbent core 62 via its core wrap 16 (acquisition layer to core wrap bond 78). If no acquisition layer 64 is present, or if the acquisition layer is shorter than the core wrap, the adhesive may also be used to bond the topsheet 58 to the absorbent core 62 (the absorbent core typically comprises a nonwoven core wrap 16, 16' not represented separately in the diaper pant illustration, but exemplary represented in FIG. 8 for a taped diaper as a C-wrap construction comprising a nonwoven top layer 16 and a nonwoven bottom layer 16'). The adhesive of the invention may also be applied e.g. to the elastic strands 96 when these are disposed between the inner belt 94 and outer belt 92, as is known in the art, and to any other adhesive bonds even not represented in the Figures. This also has the advantages of reducing the number of adhesive raw materials necessary for the fabrication of the diaper, thus reducing complexity and costs.

Taped Diaper 20'

The present invention is also applicable to taped diapers which, unlike pants, comprise a pair of tapes 41 on one side of the transversal axis T2 (typically the back side) that can be refastenably attached to a landing zone 44 on the other side of the diaper (typically disposed on the front side of the diaper). This fastening system used in taped diapers allow to close the diaper around the waist and legs of the wearer. Once the diaper needs changing, the tapes can be opened and the diaper is then easily removed. An exemplary taped diaper 20' is represented in FIGS. 5-8. FIG. 5 is a perspective view of the exemplary diaper in a closed state as it would appear when worn by a wearer. This taped diaper 20' is shown for illustration purpose only as other taped diaper construction exist. The Figures are used herein as illustration of one way to carry out the invention and are not limiting the scope of the claims, unless specifically indicated to do so.

The taped diaper typically comprises a front edge 10, a back edge 12, and two longitudinally-extending side (lateral) edges 13, 14. The front edge 10 is the edge of the article which is intended to be placed towards the front of the user when worn, and the back edge 12 is the opposite edge, and together form the waist opening of the diaper. The lateral edges 13, 14 respectively form the two leg openings when the diaper is closed. The topsheet 24, the backsheet 25, the absorbent core 28 and the other article components may be assembled in a variety of well-known configurations, in particular by gluing, fusion and/or pressure bonding. The absorbent articles of the invention may comprise any typical layers and components used in absorbent products of the diaper type, and which are not necessarily represented in the simplified FIGS. 5-8. The taped diaper can also be notionally divided by a longitudinal centerline L2 and a transversal centerline T2. The tapes 41 are placed on a different side of the T2 than the landing zone 44. The longitudinal axis and the traversal axis crosses at a point M that can be designated as the middle of the diaper.

The taped diaper 20' thus includes a fastening system comprising the tapes 41 and a landing zone 44. The landing zone is the component of the taped diaper which is adapted for receiving and engaging with the tapes 41. When fastened, the fastening system interconnects the front waist region and the rear waist region resulting in a waist circumference that encircles the wearer during wear of the absorbent article. Various fastening systems have been suggested in the art, but typically the principle is based on the hook-and-loop principles known from Velcro® attachment systems. A particular example of hooks (types and sizes) and landing zones is disclosed in WO 2016/060922 (Jennewein et al.). Typically, the male elements (hooks) are disposed on the tapes and the female elements (loops) on the landing zone. The tapes 41 are typically attached to the back ears 40, and the landing zone 44 is a discrete piece of material, typically rectangular, that is attached to the backsheet at the front part of the article, close to the front waist edge 10. The back ears 40 are typically a stretchable laminate comprising an elastic film laminated on each side to a nonwoven cover.

While the adhesive claimed may be used for a variety of bonds in a taped diaper, the invention is particularly useful to make to the bond between the landing zone 44 and the backsheet nonwoven cover 42, which is itself adhesively bonded to the impermeable backsheet film 60. In taped diapers, the backsheet film 60 and the backsheet outer cover 42 are typically coterminous so that the landing zone 44 is adhesively bonded to outer cover nonwoven 42. This landing zone to backsheet bond is submitted to elastic peel creep force along the circumference of the diaper through the tapes 41, as the elastic back ears 40 are attached to the tapes 41.

This landing zone to backsheet bond is particularly challenging with regards to the application process (application of the adhesive onto the landing zone, cut & slip process steps using a vacuum, difficult tension control, long distance between application point and combining point). As a result, there is a higher variation of the microscopic application pattern, particularly with regards to the transfer of the adhesive from the first to the second substrate (outer cover NW), and thus the coating of the fibers of the second substrate. The claimed adhesive was found to have the right intrinsic strength related properties (G', Yield Stress and Toughness) which are more forgiving to variations in the quality of the transfer to the second substrate at different lines and variations in the quality of the coating of the fibers of the second substrate. Imperfect coating of the fibers can be compensated by the superior intrinsic strength related properties of the adhesive.

Another possible application of the adhesive claimed is the bond 76 between topsheet 58 and acquisition layer 64. This is as well a challenging bond with regards to the application process: the adhesive is typically applied via slots onto the topsheet as the primary substrate. The diameter of the acquisition layer fibers is significantly larger than the diameter of the topsheet fibers (e.g. about 50 μm versus about 20 μm), which makes it more difficult to enwrap these fibers with adhesive. In addition, the acquisition layer is typically a very lofty substrate with a low bulk density (to fulfill its function of temporary liquid storage). Therefore, only a small fraction of the acquisition layer fibers is available on the surface to form a bond when both substrates are combined. Therefore, an intrinsically stronger adhesive will also compensate to some extent for the variations in the quality of transfer to the second substrate in this bond, without the need to increase the basis weight of the adhesive. If the topsheet is partially separated from the acquisition layer in use, it will stick to the baby's buttock, which is perceived as a negative experience by the consumer.

The adhesive claimed may thus also be used to form a topsheet to acquisition layer bond 76. As indicated previously, the adhesive claimed may also be used to adhesively bond the acquisition layer 64 to the core wrap bond 16 (acquisition layer to core wrap bond 78). The absorbent article may comprise one acquisition layer (as represented) but may also comprise an acquisition-distribution system, comprising an acquisition layer and a distribution layer. In such case the adhesive claimed may also be used to adhesively bond the acquisition layer and the distribution layer together. While these bonds involving the topsheet, acquisition/distribution layer(s) and core wrap are not typically submitted to strong peel creep forces in usage, unlike the landing zone to core cover bond, the adhesive claimed may still provide stronger bonds than conventional construction adhesives of the prior art between these layers. As discussed previously, the adhesive of the invention may also be used to bond the topsheet to the core wrap directly, either in these portions of the core wrap where the acquisition layer is not present or for these diapers where there is no acquisition layer. The adhesive of the invention may also be used for making any core stabilization bonds (discussed below with reference to FIG. 8), as long as the article comprises at least one nonwoven-nonwoven adhesive bond other than a core stabilization bond. Additionally, reduced complexity is achieved by using the same glue material for different adhesive bonding.

Adhesives

The present invention is applicable to any adhesives having a high value for the Toughness parameter (at least 11 MJ/m$^3$ at 37° C., and preferably at least 22 MJ/m$^3$ at 37° C.) and Yield Stress parameter (at least 0.7 MPa, and preferably at least 1.0 MPa at 37° C.) and optionally a high Storage Modulus G' (at least 3 MPa at 37° C., and preferably at least 7.5 MPa at 37° C.). The method (extensional rheology) used to measure Toughness and Yield Stress enables to screen adhesives with regards to their resistance to large strains, which occur under the real load case in use, as opposed to standard rheological adhesive tests like oscillatory rheology (yielding e.g. the storage modulus G'), which only investigates the behavior of adhesives under small deformations. Toughness and Yield Stress therewith provide critical complementary information over the storage modulus, which only describes the elastic resistance to initial small deformations and is indicative of the "stiffness" of an adhesive. The adhesive of the invention is typically a hotmelt adhesive.

The inventors found that a combination of defined minimum values of Toughness and Yield Stress is able to predict that a polyolefin-based adhesive has sufficient intrinsic strength for a construction bond, specifically a nonwoven-nonwoven bond with demanding in-use load requirements, specifically high peel creep requirements. Both parameters are available from the same measurement. The inventors also found that the storage modulus G', for which a different method is needed, can be used as a complementary third parameter for the selection, which also advantageously has a minimum value. Summing-up, the successful adhesives according to the present invention have 1) a high Toughness, i.e. ability to dissipate deformation energy over large deformations up to failure, 2) a high Yield Stress, i.e. plastic deformation only starting after the adhesive has experienced a high stress, and 3)—optionally—also a high stiffness.

The inventors found that specifically the Toughness parameter is predictive of peel creep resistance in construction bonds and creep resistance in constant displacement tests as used for elastic attachment adhesives. The inventors also found that the Toughness parameter is indicative of the usage reduction potential of an adhesive. The higher the Toughness parameter, the less usage of the adhesive is possible for an adhesive, without compromises in creep resistance. While the inventors believe that there is no theoretical upper limit to the Toughness (e.g. up to 60 MJ/m$^3$), there may be an upper limit to yield stress at 37° C. (around 20 MPa) and for G' at 37° C. (around 50 MPa) as of which the adhesive may become too brittle.

The adhesive may be typically applied according to any adapted techniques in the bond area at an average basis weight of from 0.5 g/m$^2$ to 30 g/m$^2$, in particular from 1.5 g/m$^2$ to 25 g/m$^2$, more particularly from 2 g/m$^2$ to 20 g/m$^2$. Hotmelt adhesives can be applied by contact applicators such as slot glue applicator, or non-contact applicators such as spray or spiral applicators, as is known in the art. Slot glue applicators apply the adhesives in a series of slots in the machine direction separated by gaps. Typically, the slots width is the same as the gap width, for example 1 mm, but this is of course not limiting. The average adhesive basis weight as used herein is calculated by dividing the total amount of glue by the whole bonding area, including any gaps between the glue slots, as well as any spaces between spirals glues, as is usual in the art.

While not wishing to be bound by theory, the inventors believe that in order to provide for strong bonds between a first nonwoven and a second nonwoven, the adhesive should enable the right microscopic pattern in the bond area, which can be described as a dual row entanglement of adjacent fibers from both nonwovens. Ideally, most of the fibers is embedded by 360°, or at least by 180°. This creates a mechanical lock in which the fibers are cemented. The inventors found that the combination of such mechanical lock provided by such structure in combination with the high Toughness of the adhesive enables a bond which is resistant against peel creep under in-use conditions.

The adhesives of the invention are not limited to a particular chemistry. In its simplest form, the adhesive of the invention may consist of a polymer and a tackifier. The tackifier may be a single tackifier, or a blend of tackifiers as discussed further below. A particular adhesive composition comprising 84% by weight of Licocene PP 2502 (a metallocene-technology based propylene-ethylene-copolymer) and 16% by weight of a tackifier (Eastotac Resh H-100L or Escorez 5300) was formulated and found to have the required properties, as shown in the experimental section below.

Adhesives comprising propylene-based polymers and tackifiers as described in US 2014/0358100 A1 (H. B. Fuller, Remmers et al.), especially examples 2 and 4 of this publication, are also believed to be useful as adhesives of the present invention. This disclosure indicates that the adhesive can be used for core stabilization bonds. Core stabilization bonds are those that insure the structural integrity of the core, such as the core wrap's longitudinal side seals and end seals, as well as any adhesive at least partially immobilizing the absorbent material within the core wrap. Core stabilization bonds do not include the bonds between the core wrap and another layer of the article such as backsheet, topsheet of acquisition layer, which is not part of the absorbent core.

As taught in US 2014/0358100 A1, the adhesive may include two or three different propylene-based polymers. The propylene-based polymers may be propylene homopolymers, or one or more of the two different propylene-based polymers may be copolymers with one or more other monomers (e.g., ethylene, butene, pentene, octene, etc.). The propylene-based polymers may be based entirely on olefins, i.e., do not contain any functional groups. The propylene-based polymers may comprise greater than about 75% by weight propylene or even greater than about 80% by weight propylene. The propylene-based polymers may have a polydispersity (Mw/Mn) of less than about 5, less than about 3, or even about 2. Propylene-based polymers may have a density of no greater than about 0.89, or no greater than about 0.88.

A suitable commercial adhesive believed to be according to the teaching of this disclosure is NW1414 available from H.B. Fuller Company. This adhesive NW1414 has also been proposed in the past as microfibrous adhesives for superabsorbent particles, see WO 2016/149252 A1 (P&G, Stiehl et al.). The present inventors have now found that this adhesive is also particularly useful for NW-NW construction bonds with high peel creep requirement, such as those bonds indicated in the summary of the invention.

Another commercial example of adhesives meeting the required properties was found to be DM 4699, available from Henkel, which is as well a polyolefin based formulation (the exact formulation is not disclosed).

Adhesives of the invention may comprise at least one propylene-based polymer as polymeric backbone. Propylene-based polymers include polypropylene homopolymers, propylene-ethylene copolymers, and mixtures thereof. The propylene-based polymer(s) may be the main component by weight of the adhesive, which may comprise at least 50% of the propylene-based polymer(s) by weight of the adhesive composition. The adhesive may in particular comprise at least 60% of the propylene-based polymer(s), by weight of the composition.

While the polymers indicated above (polypropylene homopolymers, or propylene-ethylene copolymers) can be generally used to form such inter-fibrous locking, the present inventors have found that not all such polymers provide the desired creep resistance properties between two nonwoven substrates. The inventors have found that the adhesive composition should further have certain mechanical properties designated as Toughness and Yield Stress at usage temperature (measured at 37° C.), which will be illustrated below in the form of different examples.

Suitable metallocene-catalyzed propylene-ethylene copolymers are commercially available from Clariant under the polymer range Licocene®, with a broad range of properties such as molecular weight, viscosity, crystallinity, etc. US 2016/053149 A1 assigned to Clamant also describes suitable co-polymers and on page 5 indicates that these examples were produced by the processes indicated in EP 571882. For a given catalyst system and given comonomer ratio, the molecular weight was regulated via the hydrogen partial pressure as molar mass regulator.

Crystallinity of the polymer, in particular of the propylene-based polymer is believed to be a contributor to the Toughness. The propylene-based polymer, in particular a propylene-ethylene copolymer, is advantageously semi-crystalline, having an enthalpy of fusion of at least 20 J/g, as measured according to the Enthalpy of Fusion Measurement Method described herein. However too high crystallinity can make the adhesive composition brittle, so the enthalpy of fusion may be advantageously less than 100 J/g, in particular less than 50 J/g, as measured according to the Enthalpy of Fusion Measurement Method described herein.

Commercial example of suitable propylene-ethylene copolymers is Clariant's Licocene® PP 2502, which has a measured enthalpy of fusion of 29.4 J/g, or Clariant's Licocene® 3602 which has a measured enthalpy of fusion of 35.0 J/g. On the other hand, Licocene® PP 1502 which has a measured enthalpy of fusion of 15.1 J/g or Licocene® PP 1602 which has a measured enthalpy of fusion of 16.7 J/g, are believed to be not crystalline enough to be used alone.

The adhesive may comprise a first propylene-based polymer that has a Mw (molecular weight) of at most about 75,000, at most about 60,000, at most about 50,000, or between about 30,000 and about 70,000, wherein the first propylene-based polymer may be present in the overall composition in an amount of at least about 20%, 25%, or 30% by weight, or from about 15% to about 50% by weight, or from about 25% to about 45% by weight. Exemplary first polymers may include LICOCENE PP1602 and LICOCENE PP2602 both available from Clariant International Ltd. (Muttenz, Switzerland) and L-MODU X400S and L-MODU X600S available from Idemitsu Kosan Co., Ltd. (Japan).

The composition may also comprise a second propylene-based polymer that has a Mw of at least about 100,000, at least about 125,000, at least about 150,000, or between about 125,000 and about 400,000, or between about 150,000 and about 250,000. The second propylene-based polymer may be present in the composition in an amount of at most about 20% by weight, at most about 15%, by weight, at most about 8% by weight, or from about 2% by weight to about 15% by weight, or from about 3% by weight to about 10% by weight. Exemplary second polymers may include VISTAMAXX 6202 and VISTAMAXX 6102 available from ExxonMobil Chemical (Houston, Tex.) and VERSIFY 3300 available from Dow Chemical Company (Houston, Tex.). The total propylene-based polymer content of a composition may be at least about 20% by weight, at least about 25% by weight, at least about 30% by weight, at least about 35% by weight, or from about 35% by weight to about 50% by weight.

The composition may include a third polymer, such as a styrenic block copolymer, which may be hydrogenated. Useful hydrogenated styrene block copolymers include, e.g., styrene-ethylene/butadiene-styrene block copolymer, styrene-ethylene/propylene-styrene block copolymer, styrene-ethylene/ethylene-propylene-styrene block copolymer, and combinations thereof. The styrenic block copolymer may have a styrene content of less than about 20% by weight, less than about 18% by weight, or even less than about 15% by weight. The styrene block copolymer may also have a Melt Flow when tested according to ASTM 1238 (230° C., 5 kg) of less than about 25 g/10 min, less than about 20 g/10 min, less than about 10 g/10 min, or even less than about 5 g/10 min. Exemplary hydrogenated styrene block copolymers are commercially available under a variety of trade designations including, e.g., the SEPTON series of trade designations from Kuraray Co., Ltd (Houston, Tex.) including, e.g., SEPTON 52063 and 52007 hydrogenated styrene-isoprene-styrene block copolymers, the KRATON G series of trade designations from Kraton Performance Polymers Inc. (Houston, Tex.) including, e.g., KRATON G 1645M, KRATON G 1657 styrene-ethylene/butadiene-styrene block copolymers. The materials may include no greater than about 20% by weight, no greater than about 15% by weight, from about 2% to 20% by weight, or even from about 5% to 15% by weight of the third polymer.

The adhesive composition may comprise a blend of two, three or more polymers, in particular the adhesive composition may comprise:

from about 15% to about 45% of a single-site catalyzed and propylene-based low basis weight first polymer(s) having a Mw of from about 30,000 to about 75,000; and
from about 2% to about 15% of propylene-based second polymer(s) having a Mw from about 100,000 to about 400,000, and wherein the second polymer has a density of no greater than 0.89.

The low molecular weight metallocene-catalyzed polymer may further comprise a blend of two co-polymers, in particular:

a first low molecular weight metallocene-catalyzed propylene-ethylene copolymer having an enthalpy of fusion below 20 J/g; and
a second low molecular weight metallocene-catalyzed propylene-ethylene copolymer having an enthalpy of fusion above 20 J/g.

The first low molecular weight metallocene-catalyzed propylene-ethylene copolymer has an enthalpy of fusion of less than 20 J/g, in particular from 5 J/g to 15 J/g, and may described as low-crystalline. A commercial example of the first copolymer is Licocene® PP 1602 from Clariant. Licocene PP 1602 is sold as granules and is described as a low melting, metallocene-technology based propylene-ethylene copolymer, which exhibits a low degree of crystallinity. The Mp of Licocene® PP 1602 was measured to be 75,900 g/mol and its enthalpy of fusion of 16.7 J/g (see measurement method below). Another example is Licocene® PP 1302. The Mp of Licocene® PP 1302 was measured to be 24,100 g/mol and its enthalpy of fusion of 11.8 J/g.

The second low molecular weight metallocene-catalyzed propylene-ethylene copolymer has a higher enthalpy of fusion than the first copolymer, of at least 20 J/g, in particular from 25 J/g to 45 J/g. Polymer in this range can be described as semi-crystalline. The second copolymer may have a Mp in the range of from 50,000 g/mol to 130,000 g/mol, or from 60,000 g/mol to 110,000 g/mol. A commercial example of the second copolymer is Licocene® PP 3602 which is sold as granules and is described as a low crystalline metallocene-catalyzed propylene-ethylene copolymer. Licocene® 3602 has a measured enthalpy of fusion of 35.0 J/g.

The first and second copolymers described above may be typically blended at a weight ratio of 10:90 to 90:10, for example 50:50 or 2:1 or 1:2. Blending two lower molecular weight copolymers with different crystallinity was found to enable low stiffness (as specifically required for NW-Film construction bonds), while still maintaining high toughness (as generally required for NW-NW and NW-Film construction bonds).

An example is a blend of Licocene® 3602 and Licocene® 1602, which are both propylene-ethylene copolymers from Clariant. Licocene 3602 is a relatively highly crystalline polymer while Licocene 1602 has a medium crystallinity.

The enthalpy of fusion is however believed not to be the only relevant factor to predict good peel creep resistance of the adhesive composition comprising the polymers. For example, Idemitsu's L-MODU S-410 has a measured enthalpy of fusion of only about 2 J/g but is believed to still be able to provide good performance. The inventors believe that the adhesive's performance is driven by a relatively high Toughness, as measured as indicated below. This Toughness is believed to be driven by the homopolymer nature of L-MODU 5410 as well as the relatively higher molecular weight of the polymer (45.000 g/mol). Toughness is believed to be increased with the molecular weight of the polymer.

Propylene-based polymers comprise propene monomer units. In copolymers, the percentage of propene monomer units may range for example from 50% to 99% by weight of the copolymer. If the percentage of propene monomer units is not known, it may be determined by a suitable method, such as nuclear magnetic resonance or infrared spectroscopies, as known to those of skill in the art.

The polymers of the invention can be prepared using a metallocene catalysts. The polymer can be for example prepared by the methods described in US 2016/0053149 A1 ("Ready-to-use hot melt adhesive having an improved property profile"). The polymer can be prepared into a final polymeric adhesive by heating the primary polymer to elevated temperatures (e.g., about 135 to about 175° C.) that melts the polymer. Once molten, other ingredients (tackifier (s), and e.g. additives or other polymers components) can be added to the primary polymer. A mixer can be used to mix the components together into a final adhesive composition. See for example U.S. Pat. No. 5,723,546, which discloses such blending.

The Toughness of the formulation can be significantly increased when a polyolefin having a high peak molecular weight Mp of from 130,000 g/mol to 700,000 g/mol, is used. The high molecular weight polyolefin may have a peak molecular weight which is at least greater by 10,000 g/mol than the (highest for blends) peak molecular weight of the low molecular weight metallocene-catalyzed polymer(s) described above, in particular at least 20,000 g/mol, or even at least 50,000 g/mol greater. The high molecular weight polyolefin may in particular have a peak molecular weight of from 140,000 g/mol to 410,000 g/mol, or from 150,000 g/mol to 360,000 g/mol.

The inventors have found that, surprisingly, the addition of a longer molecular weight polyolefin significantly increases the strain hardening of the blend besides increasing the elongation at break, which in combination results in a significantly higher Toughness of the formulation. Strain hardening is believed to be a "self-repairing mechanism of the blend when being strained, which avoids early rupture.

The high molecular weight polyolefin may be advantageously comprised of a single material to simplify the compounding and formulation of the hotmelt composition, but it is not excluded that it may also be a blend of individual material falling under this definition. The hotmelt composition may typically comprise from 1% to 20% of such a high molecular weight polyolefin (or mixture thereof), by weight of the hotmelt composition, in particular from 2% to 15%, especially from 5% to 10% by weight of the hotmelt composition. It is believed that already small additions of the longer molecular weight polyolefins can significantly boost the strain hardening and hence the Toughness. More than 10% may on the other hand increase the viscosity. Toughness, strain hardening and Elongation at break are measured and observed in the Extensional Test Method, submitting the adhesive to large deformations, as relevant when the bond is subjected to forces in use.

The high molecular weight polyolefins may be a homopolymer or a copolymer. The copolymer may comprise different alpha olefin monomers such as ethylene, propylene, 4-methyl-1-pentene, pentene-1, 2-methylpentene-1, 3-methylbutene-1, heptene-1, dimethylpentene-1, trimethylbutene-1, ethylpentene-1, methylpentene-1, trimethylpentene-1, methylethylpentene-1, 1-octene, diethylbutene-1, propylpentane-1, decene-1, methylnonene-1, nonene-1, trimethylheptene-1, methylethylbutene-1, dodecene-1, and hexadodecene-1, and combinations thereof.

Nonlimiting examples of commercially available high molecular weight polyolefins are Affinity EG 8200G, Engage 8200, Infuse 9817, Vistamaxx 3000, Vistamaxx 6102, Vistamaxx 6202, Vistamaxx 6502, VERsify 4200, VERsify 4301.

The high molecular weight polyolefin may be in particular a propylene-ethylene copolymer. The high molecular weight polyolefin may also be a metallocene-catalyzed based copolymer, in particular a metallocene-catalyzed propylene-ethylene copolymer. The high molecular weight polyolefin may in particular be a propylene-ethylene copolymer comprising greater than 80 wt. % of polypropylene units with isotactic stereochemistry. Examples of such copolymers are commercially available as the Vistamaxx series from ExxonMobil. For example, Vistamaxx 6202 and Vistamaxx 6502 are sold as pellets and are described by their manufacturer as primarily composed of isotactic propylene repeat units with random ethylene distribution, produced using a metallocene catalyst technology. Vistamaxx 6202 and 6502 were used as high molecular weight polymer in the formula examples below. Vistamaxx 6502 has the lowest viscosity, and thus the least impact on increasing the viscosity of the total composition.

Tackifier(s)

The adhesives of the invention comprise at least 5% by weight of the adhesive of a tackifier (or a mixture of tackifiers). The word tackifier is used in the singular, but unless otherwise stated, this means "one or more tackifier", as blends of tackifiers may also be used. The adhesive composition may comprise from 10% to 70%, in particular from 20% to 65%, or from 25% to 60%, or 26% to 60%, or 30% to 60% by weight of the composition, of the tackifier(s). Tackifiers otherwise called "tackifier resins" or "tackifying resins" are low-molecular weight compounds (oligomers) that are added to adhesive formulations to improve tack and peel adhesion materials. Usual tackifiers known in the art may be used in the present invention. Typical tackifiers are thermoplastic materials stable at least up to 200° C., being amorphous glasses at room temperature, and having a Tg higher than 50° C., preferably comprised between 80° C. and 125° C. Tackifiers typically have a molecular weight comprised between 500 and 2000 Daltons.

Tackifiers are in general organic chemicals with polycyclic structure. Commonly used tackifiers are selected from rosin resins and their derivatives (rosin esters), hydrocarbon resins produced from petroleum-based by-products of naphtha crackers, and terpene resins (modified or not). Hydrocarbon resins may be aliphatic, cycloaliphatic and aromatic resins (in particular C5 aliphatic resins, C9 aromatic resins, and C5/C9 aliphatic/aromatic resins), and may be optionally hydrogenated hydrocarbon resins.

Exemplary tackifiers include aliphatic hydrocarbon resins, aromatic modified aliphatic hydrocarbon resins, hydrogenated poly-cyclopentadiene resins, poly-cyclopentadiene resins, gum rosins, gum rosin esters, wood rosins, wood rosin esters, tall oil rosins, tall oil rosin esters, poly-terpenes, aromatic modified poly-terpenes, terpene-phenolics, aromatic modified hydrogenated poly-cyclopentadiene resins, hydrogenated aliphatic resins, hydrogenated aliphatic aromatic resins, hydrogenated terpenes and modified terpenes, and hydrogenated rosin esters. Particularly suitable tackifiers are rosin (and its derivatives) resins and hydrogenated hydrocarbon tackifiers, which are solid at room temperature.

The benefits of using tackifiers include (i) increasing the open time of the adhesive, which enables in general a better transfer to the second substrate in the lamination process, particularly when the open time of the process (defined as the distance between applicator and combining point divided by the line speed) is short, and (ii) enabling to increase the polarity of the adhesive, which contributes to increase the bond strength to more polymer substrates (like e.g. polyester fibers), particularly for bonds in which an optimum entanglement of the fibers is difficult to achieve.

In some embodiments, the tackifier has a Mw below 5,000 and a Tg above room temperature. Suitable classes of tackifier include, for example, aromatic, aliphatic and cycloaliphatic hydrocarbon resins, mixed aromatic and aliphatic modified hydrocarbon resins, aromatic modified aliphatic hydrocarbon resins, and hydrogenated versions thereof; terpenes, modified terpenes and hydrogenated versions thereof; natural rosins, modified rosins, rosin esters, and hydrogenated versions thereof, and combinations thereof.

Suitable commercial tackifiers include, for example, the ESCOREZ series of trade designations from Exxon Mobil Chemical Company (Houston, Tex.) including ESCOREZ 5400 and ESCOREZ 5600, the EASTOTAC series of trade designations from Eastman Chemical (Kingsport, Tenn.) including EASTOTAC H-100R and EASTOTAC H-100L, and the WINGTACK series of trade designations from Cray Valley HSC (Exton, Pa.) including WINGTACK 86, WINGTACK EXTRA, and WINTACK 95 and the PICCOTAC and KRISTALEX series of trade designations from Eastman Chemical Company (Kingsport, Tenn.) including, e.g., PICCOTAC 8095 and KRISTALEX 3100.

The adhesive may also optionally comprise additives such as one or more antioxidant, UV stabilizer, brightener, colorant, fragrance etc. The adhesive may comprise less than 5% by weight of such additives. Any antioxidant known to a person of ordinary skill in the art may be used in the adhesion composition.

Other Components of the Articles

As indicated previously, the absorbent articles of the invention whether as pant diaper 20 or taped diaper 20' can comprises any of the typical components found in these absorbent articles. The absorbent article comprises a liquid permeable topsheet 58 on its wearer-facing side, a liquid impermeable backsheet film 60 on its garment-facing side and an absorbent core 62 between the topsheet and the backsheet (the outline of which is shown in dotted line in FIG. 2 and FIGS. 6-7). An absorbent core may be omitted for swimming pants. The topsheet typically forms the majority of the wearer-contacting surface of the article and is the first layer that the body exudates contact. The topsheet is liquid permeable, permitting liquids to readily penetrate through its thickness. Any known topsheet may be used in the present invention, typically a nonwoven which may be apertured or not. Alternatively an apertured formed film may be used but this is unusual in diaper applications. The backsheet typically comprises a fluid impermeable plastic film 60, which may be printed with a decorative backsheet pattern, and a low basis weight nonwoven outer cover 42 glued to it. The nonwoven outer cover 42 provides a nicer touch and appearance to the backsheet.

Figure 8:
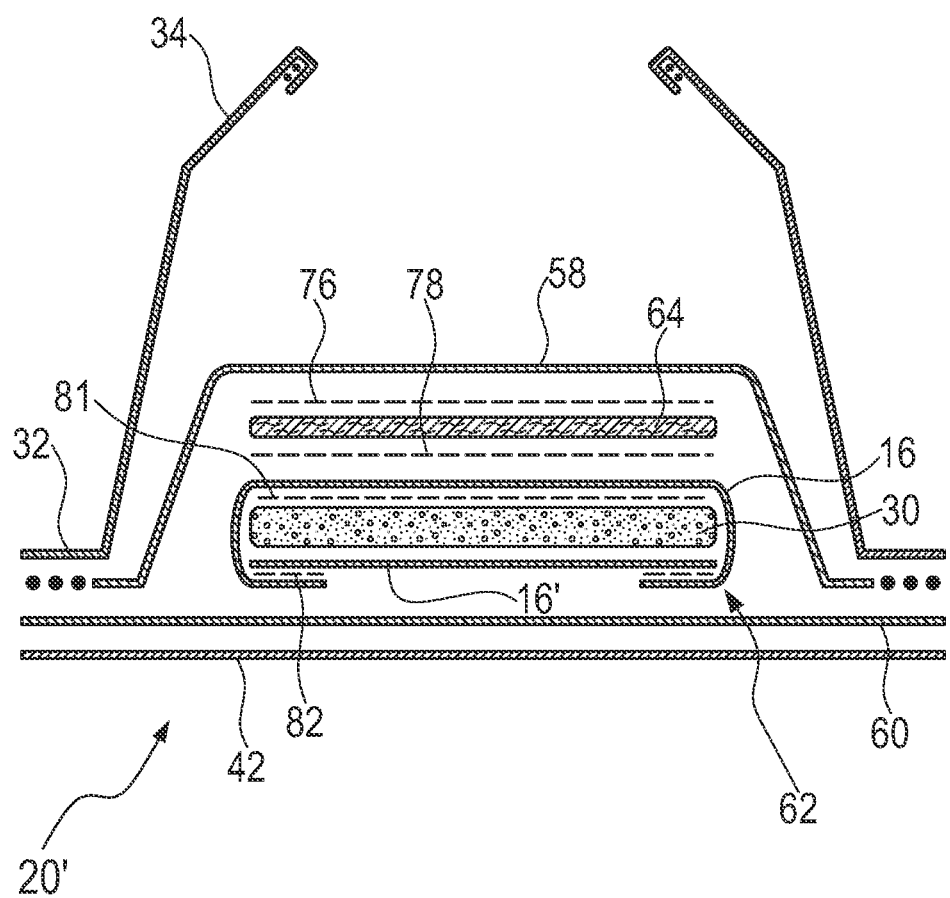
FIG. 8 is an exemplary cross-sectional view of a diaper as in FIG. 7.

The absorbent article may also comprise a fluid acquisition layer 64 and/or a fluid distribution layer between the topsheet and the absorbent core, as well as other typical diaper components such as elasticized gasketing cuffs 32, upstanding barrier leg cuffs 34, which are represented only in FIG. 8, but are present in most diapers including in the chassis of pant diapers. The absorbent article may also comprise other usual components, if it is desired to increase the performance of the article, such as transverse barrier cuffs, front and/or back elastic waistbands (for taped diapers), a lotion application on the topsheet, longitudinally extending channels in the core and/or the distribution layer, a wetness indicator, etc. all these components have been described and exemplified in the art and are not further detailed herein. More detailed disclosures of example of such components are for example disclosed in WO 201493323, WO 2015/183669 (both Bianchi et al), WO 2015/031225 (Roe et al.) or WO 2016/133712 (Ehrnsperger et al.) to name a few.

The absorbent core 62 typically comprises an absorbent layer 30 comprising superabsorbent particles sandwiched between the top layer 16 and the bottom layer 16' of a core wrap, as illustrated in FIG. 8. The core is depicted more schematically for the pant diaper in FIGS. 3-4 but absorbent cores used in taped diapers can be of the same construction as core in the pant diapers. The absorbent core typically comprises core stabilization bonds, which help maintaining the structural integrity of the core. Core stabilization bonds are the core wrap's longitudinal side seals 82 as well as core end seals if present (not represented), as well as any adhesive at least partially immobilizing the absorbent material within the core wrap, such as an auxiliary glue 81 applied on the inner side of the top layer or bottom layer of the core wrap. However, core stabilization bonds do not include the bonds between the core and another layer of the article such as backsheet, topsheet of acquisition layer which is not part of the absorbent core. For simplicity, not all adhesives bonds are shown in the Figures, for example the backsheet laminate bond between the film 60 and the outer core nonwoven 42 is not shown.

EXAMPLES

Table 1 discloses the enthalpy of fusion in J/g of some commercially available polymers that may be used in the invention:

TABLE 1

| | Enthalpy of Fusion |
|---|---|
| Licocene PP 1302 | 11.8 |
| Licocene PP 1602 | 16.7 |
| Licocene PP 2502 | 29.4 |
| Licocene PP 3602 | 35.0 |

The following adhesive compositions were formulated (all figures in % weight) as indicated in Table 2. Licocene® are propylene-ethylene copolymers from Clariant. Eastotac and Escorez are tackifiers available from Eastman and ExxonMobil respectively. Vistamaxx® is a polypropylene polymer from ExxonMobil primarily composed of isotactic propylene repeat units with random ethylene distribution.

TABLE 2

| Example | Licocene PP 2502 | Licocene PP 1602 | Licocene PP 3602 | Eastotac Resh H-100L | Escorez 5300 | Vistamaxx 6502 |
|---|---|---|---|---|---|---|
| 1 | 50 | | | 40 | | 10 |
| 2 | | 46.7 | 23.3 | 20 | | 10 |
| 3 | | 33.3 | 16.7 | 40 | | 10 |
| 4 | | 36.7 | 18.3 | 40 | | 5 |
| 5 | | 40 | 20 | 40 | | |
| 6 | | 33.3 | 16.7 | 40 | | 10 |
| 7 | | 40 | 24 | 26 | | 10 |
| 8 | 84 | | | 16 | | |
| 9 | 84 | | | | 16 | |
| 10 | 90 | | | 10 | | |

Experimental Measurements

The Toughness, Yield Stress, and G' of exemplary adhesives as well as commercial adhesives were measured as indicated in the test methods section below and the results summarized in the Table 3 below. Among the commercial adhesives, NW1414 and DM4699 were found to meet the criteria of the invention (Table 3), unlike D3166, DM3800, DM3522 and DM3442 which are commercial polyolefin-based adhesives used in absorbent articles (state of the art).

TABLE 3

| Adhesive (Source) | Toughness [MJ/m$^3$] @ 37° C., 1 s$^{-1}$ | Yield Stress [MPa] @ 37° C., 1 s$^{-1}$ | G' [MPa] @ 37° C. cold to hot |
|---|---|---|---|
| Requirement | ≥11 | ≥0.7 | ≥3.0 (optional) |
| Preferred Requirement | ≥22 | ≥1.0 | ≥7.5 |
| Example 1 | 13.8 | 3.2 | 12.1 |
| Example 2 | 22.4 | 1.5 | 5.6 |
| Example 3 | 43.5 | 1.2 | 3.9 |
| Example 4 | 22.5 | 1.3 | 4.3 |
| Example 5 | 20.6 | 3.6 | 5.5 |
| Example 6 | 27.1 | 1.3 | 3.1 |
| Example 7 | 31.4 | 2.9 | 7.7 |
| Example 8 | 11.5 | 5.0 | 17.9 |
| Example 9 | 11.5 | 4.4 | 18.1 |
| Example 10 | 7.5 | 10.4 | 19.8 |
| NW 1414 (HB Fuller) | 23.5 | 1.0 | 8.9 |
| DM 4699 (Henkel) | 40.8 | 3.4 | 24.8 |
| D 3166 (HB Fuller) (comparative) | 2.8 | 0.1 | 0.4 |
| DM 3800 (Henkel) (comparative) | 20.7 | 0.5 | 2.3 |
| DM 3522 (Henkel) (comparative) | 7.6 | 0.4 | 0.7 |
| DM 3442 (Henkel) (comparative) | 4.7 | 0.2 | 1.3 |
| Licocene 2502 (Clariant) (comparative) | 8.7 | 0.10 | 33.5 |

Some of these adhesives were slot coated over the full area at a basis weight of 15.4 g/m$^2$ between two nonwovens representative of a landing zone to backsheet core cover bond in a converting line. The samples were hanged with one nonwoven maintained in vertical position and the other nonwoven attached to a weight of 150 g. The delamination time ("Peel Hang Time") was measured for 45 mm bond length samples having a width of 40 mm for some of these adhesives and is representative of the resistance of the adhesives to peel creep forces.

TABLE 4

| Adhesive (source) | Peel hang time at 22° C. in minutes (max 500 minutes) |
| --- | --- |
| NW 1414 (HB Fuller) (inventive) | 500 |
| D 3166 (HB Fuller) (comparative) | 10.4 |
| DM 3800 (Henkel) (comparative) | 41.7 |

This first set of data shows that NW1414 was considerably better for NW-NW Bonds than the comparative examples. The measurement was stopped after 500 minutes without delamination for the inventive example.

In the below examples, the adhesives were slot coated with 1 mm wide stripes/1 mm gap between the stripes at a specified basis weight (on the stripes) between two nonwovens. As only half of the area was covered, the average basis weight over the whole area is half of the basis weight on the stripes. The Peel Hang Time was measured for the different 6 mm bond length samples having a width of 25.4 mm, and an applied weight 150 g.

TABLE 5

| Adhesive | Average Basis weight [g/m$^2$] | Peel Hang Time at 22° C. in minutes (max 1000 minutes) |
| --- | --- | --- |
| NW 1414 (inventive) | 4 | 1000 |
| NW 1414 | 3.6 | 938 |
| DM4699 (inventive) | 2.8 | 1000 |
| DM4699 | 2 | 1000 |
| Ex 7 (inventive) | 2 | 1000 |
| Ex 7 | 1 | 284 |
| DM 3800 (comparative) | 4 | 160 |

This second set of data shows that the inventive adhesives have better performance against peel creep forces even at lower basis weight than conventional prior art adhesive.

Test Methods

Extensional Test Method

The Extensional Test Method is used to determine the Yield Stress and the Toughness for a specimen of a polymer composition. A thin film specimen formed of polymer composition is analyzed with a rotational rheometer fitted with a specialized fixture with counter rotating rollers, and the stress associated with extensional strain imparted is measured and recorded.

Instrumental setup A rotational rheometer (ARES G2, TA Instruments, New Castle, Del., USA, or equivalent) is fitted with a fixture that has counter rotating cylindrical rollers specifically designed for the interrogation of extension deformation of films. An example of a suitable fixture is the Extensional Viscosity Fixture, or EVF (EVF, TA Instruments, or equivalent). The rheometer is further fitted with a forced-convection oven FCO (FCO, TA Instruments, or equivalent) and cooling system (ACS 2, TA Instruments, or equivalent) capable of controlling temperate from at least −50 to 250° C. to a within a tolerance of 0.5° C.

Specimen Preparation

Approximately 6 g±2 g of the polymer composition is placed in a circular polytetrafluoroethane (PTFE) bowl with a flat bottom (diameter of 60 mm±2 mm) and introduced into a vacuum oven held at 170° C. After 15 minutes at ambient pressure, the pressure is lowered to 10 mbar, and the polymer composition is subsequently held at 170° C. and at 10 mbar for 45 minutes to remove air bubbles from the polymer composition. If 170° C. is insufficient to melt the polymer compositions a temperature 30±10° C. above the melting temperature of the polymer material composition is used. The polymer composition is removed from the vacuum oven and allowed to cool to ambient lab conditions (23±2° C.) for 90±30 minutes, at which point the polymer composition is removed from the PTFE bowl and placed between 2 sheets of siliconised paper (such as product number 114918, Mondi Group, Hilm, Austria, or equivalent). A metal shim 500±30 μm in thickness is used in the heated press as a spacer to obtain a film thickness of 500 μm when pressed with a heated press at 90° C. for 60 seconds at a pressure sufficient to form a polymeric film. If 90° C. is insufficient to press a uniform flat film, a temperature approximately 10±5° C. below the melting point of the sample material composition such that the sample material composition is in a semi-solid state is used. The film is stored at least 120 hours in the laboratory at 23±2° C. prior to testing. From the film individual specimens for measurement are punched with a sample cutter to the final specimen dimensions of 20.0 mm by 10.0 mm by 500 μm.

Measurement

To secure the specimen film to the cylinders of the EVF, the cylinders are heated to 50° C. for 90±30 s in the forced-convection oven of the rheometer. After opening the oven, the specimen of polymer composition is briefly pressed onto the cylinders of the EVF to secure it to the cylinder surfaces. The specimen is placed with its length perpendicular to the axis of rotation of the cylinders. For polymer compositions, which are very stiff and do not adhere to the cylinder surface, the EVF are heated to 80° C. for 90±30 s in the forced-convection oven of the rheometer. Then a small droplet (0.03±0.01 g) of an auxiliary hotmelt adhesive is applied to each cylinder. The used auxiliary adhesive should exhibit a high stiffness (G' at 23° C. and 1 Hz of the auxiliary adhesive greater than 10 MPa) to not interfere with the measurement. The specimen of polymer composition is quickly pressed on the auxiliary adhesive on the cylinders of the EVF to fix it to the cylinder surfaces. The specimen is placed perpendicular to the axis of rotation of the cylinders.

The specimen mounted on the EVF is then placed in the forced convection oven of the rheometer for thermal conditioning and is kept isothermal at 37±0.5° C. for 300±10 s. After this time has elapsed, the specimen is mechanically conditioned. To mechanically condition the specimen, the torque transducer is zeroed, and the sample is put under a pre-stretch rate of 0.001 s$^{-1}$ for 0.30 s and then allowed to relax for 60 s (in this method, all strain is expressed in terms of Hencky strain, also known as "true strain" or "logarithmic strain.").

The measurement is performed in the FCO oven at 37° C.±0.5° C. The strain rate extension for the measurement is 1 s$^{-1}$, and the strain at maximum extension is 4.0. After measurement, the specimen is checked for rupturing. If it has ruptured, the location of the break is noted. If the rupture is approximately in the middle between the two cylinders of the EVF, the data collected are deemed acceptable. Otherwise, if the polymeric film break is at or close to the rotating cylinders, the results are discarded, and the measurement performed again on a replicate specimen.

Analysis

For the extensional stress calculation, a constant volume is assumed. From the raw torque versus angular displacement data recorded by the rheometer, extensional stress (in megapascals, or MPa) versus Hencky strain data are calculated. The data are plotted in semilogarithmic fashion with Hencky strain on the abscissa (linear scale) and extensional stress on the ordinate (logarithmic scale). A linear range is sought in this plot. If a linear range above a strain of 0.3 can be identified and this range can be fit with a positive slope with an $R^2$ value of 0.98 or greater, the value of the fitted line at a Hencky strain of zero (that is, the y-intercept), is defined as the Yield Stress, which is reported in MPa to the nearest kilopascal. Otherwise, the maximum value of extensional stress recorded during the measurement is reported as the Yield Stress, again reported in MPa to the nearest kilopascal.

The extensional stress (MPa) versus Hencky strain data calculated above are again plotted, but this time in linear fashion with Hencky strain on the abscissa (linear axis) and extensional stress on the ordinate (linear axis). The integral of extensional stress with strain (that is, the area under the extensional stress curve as a function of strain) is calculated from a strain of zero to the strain at which the sample ruptured (or, in the case it did not rupture during the measurement, to a strain of 4.0) and is reported as the Toughness, which is reported in units of megajoules per cubic meter, or $MJ/m^3$.

Oscillatory Rheometry Test Method

The Oscillatory Rheometry Test Method is used to measure the Storage Modulus G' and the Loss Factor of a polymer composition. A controlled-strain rotational rheometer (such as Discovery HR-3, TA Instruments, New Castle, Del., USA, or equivalent) capable of sample temperature control (using a Peltier cooler and resistance heater combination) with a precision equal to or exceeding 0.5° C. over at least the range of −10° C. to 150° C. The rheometer is operated in a parallel plate configuration with 20-mm stainless steel parallel-plate tooling.

A parallel plate gap of 1000 µm is initially used in the method. To compensate for thermal expansion of the tooling, the gap is set to 1000 µm, and a mapping of actual plate gap (as measured using a suitable standard test fluid) a function of temperature over the range −10° C. to 150° C. is performed. This mapping is then used throughout the determination of the Storage Modulus Parameter and the Loss Factor Parameter.

The rheometer is heated to 150° C., the polymer composition is introduced in the rheometer, the gap is set to 1050 µm, excess protruding sample is trimmed, and the gap is then set to 1000 µm. (The axial force control of the rheometer is set to 0 N and be maintained within ±0.1 N of force during the experiment, thereby thermal expansion/contraction of the sample itself is compensated by adjusting the gap in order to avoid overfilling or underfilling in addition to the abovementioned compensation of the tooling.) The rheometer is then allowed to cool to 130° C., at which point the measurement commences with temperature ramped from 130° C. to −10° C. at a constant rate of cooling of 2° C./min. The applied strain amplitude is 0.1%, and the frequency of oscillation is 1 Hz (that is, one cycle per second). The resulting oscillatory stress is recorded.

After this step, the sample temperature is set to 23° C. (temperature is ramped to this setpoint at a rate of 10° C./min), and the sample is allowed to rest for 4.0 hours at 23° C. At the end of this period, the temperature is set to −10° C. (temperature is ramped to this setpoint at a rate of 10° C./min), the sample is equilibrated for 300 seconds at −10° C., and a second oscillatory rheology measurement is conducted (0.1% strain, frequency of oscillation of 1 Hz) while temperature is ramped upward to 130° C. at a constant rate of increase of 2° C./min.

From the first decreasing temperature sweep, the storage modulus G' is calculated and recorded at 37° C., and these values are reported in Pascals (Pa) to the nearest 1 Pa as the "Storage Modulus at 100° C.". From the first, decreasing temperature sweep, the loss factor (also known as tan delta) is calculated recorded at 100° C., and this dimensionless value is reported to the nearest hundredth as the "Loss Factor at 100° C.". The storage modulus G' can also be calculated and recorded at different temperatures, for example 100° C.

Enthalpy of Fusion Measurement Method

The Enthalpy of Fusion of a hot-melt adhesive composition is determined using the Enthalpy of Fusion Test Method, which consists of performing ASTM D3418-15 with the following additional guidance. Hot-melt specimen(s) are preferably extracted from molded or pelleted raw material adhesive composition. If raw material is not available, specimen(s) of adhesive are extracted from bonds of interest in an absorbent article using techniques known to those of skill in the art. Dry nitrogen is used as the purge gas in the differential scanning calorimeter (DSC). The rate of increase of temperature in the DSC is 10° C./min, and the rate of decrease of temperature in the DSC is 1° C./min. The mass-normalized enthalpy of fusion is calculated as specified in section 11.4 based on the curve corresponding to decreasing temperature (at 1° C./min) and is reported as the "Enthalpy of Fusion" in units of joules per gram (J/g) to the nearest 0.1 J/g.

Molecular Weight

The weight-average molecular weight Mw and number-average molecular weight Mn are determined according to the standard ISO 16014.

Misc.

The claims may suitably comprise, consist of, or consist essentially of, or be substantially free of any of the disclosed or recited elements. The invention illustratively disclosed herein can also be suitably practiced in the absence of any element which is not specifically disclosed herein.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a topsheet, a backsheet, an absorbent core and at least one nonwoven-nonwoven adhesive bond other than a core stabilization bond, wherein the adhesive has a Toughness of at least 11.0 MJ/m$^3$ and a Yield Stress of at least 0.7 MPa, as measured at 37° C. according to the Extensional Test Method, and wherein the adhesive comprises at least 5% tackifier by weight of the adhesive.

2. The absorbent article according to claim 1, wherein the adhesive comprises a propylene-based polymer or a blend of propylene-based polymers.

3. The absorbent article according to claim 2, wherein the adhesive comprises at least 25% by weight of the propylene-based polymer or blend of propylene-based polymers.

4. The absorbent article according to claim 2, wherein at least one of the propylene-based polymer(s) has an enthalpy of fusion of at least 20 J/g, as measured by the Enthalpy of Fusion Measurement Method.

5. The absorbent according to claim 4, wherein the at least one of the propylene-based polymer(s) has an enthalpy of fusion of from about 20 J/g to about 50 J/g, as measured by the Enthalpy of Fusion Measurement Method.

6. The absorbent article according to claim 2, wherein the adhesive comprises, by weight of the adhesive:
   from about 15% to about 45% of a first polymer that is single-site catalyzed and propylene-based and has a Mw of from about 30,000 to about 75,000; and
   from about 2% to about 15% of a second polymer that is propylene-based and has a Mw from about 100,000 to about 400,000, and wherein the second polymer has a density of no greater than 0.89.

7. The absorbent article according claim 1, wherein the adhesive has a storage modulus G' of at least 3 MPa as measured at 37° C. according to the Oscillatory Rheometry Test Method.

8. The absorbent article according to claim 1, wherein the adhesive has a G' of from about 7.5 to about 50 MPa, as measured at 37° C. according to the Oscillatory Rheometry Test Method.

9. The absorbent article according to claim 1, wherein the adhesive is applied in a bond area at an average basis weight of from about 0.5 g/m$^2$ to about 30 g/m$^2$.

10. The absorbent article according to claim 1, wherein the adhesive has a Toughness of between about 22 MJ/m$^3$ and about 60 MJ/m$^3$.

11. The absorbent article according to claim 1, wherein the adhesive has a Yield Stress of from about 1.0 MPa to about 20 MPa.

12. The absorbent article according to claim 1, wherein the article is a pant diaper having a front region, a rear region, and a crotch region disposed therebetween; the pant diaper comprising:
   a central chassis comprising a liquid permeable topsheet, a liquid impermeable backsheet comprising a liquid impermeable film and a nonwoven outer cover, an absorbent core having a core wrap disposed between the topsheet and the backsheet, and optionally an acquisition layer;
   a waist belt disposed about the central chassis, the waist belt overlaying the backsheet to the outside thereof in the front and rear regions, the waist belt overlapping and extending transversally and longitudinally outward from the chassis;
   wherein the waist belt comprises a front belt and a rear belt, each comprising an outer belt, an inner belt and elastic strands therebetween;
   wherein the front belt has a front waist edge, and front left and right side edges; and the rear belt has a rear waist edge and rear left and right side edges, wherein respective front and rear left side edges and the respective front and rear right side edges are joined by side seam bonds, forming a waist opening and left and right leg openings;
   wherein the nonwoven-nonwoven adhesive bond is selected from one or more of:
   i) a belt panel bond, which bonds the outer belt to the inner belt;
   ii) a chassis-to-belt bond, which bonds the inner belt and the chassis;
   iii) a waist fold bond, which bonds the belt fold-over to the chassis;
   iv) the side seam bonds, which bond the side edges of the front belt and the back belt;
   v) a topsheet to acquisition layer bond;
   vi) an acquisition layer to core wrap bond; and
   vii) a topsheet to core wrap bond.

13. The absorbent article according to claim 12, wherein the adhesive nonwoven-nonwoven bond comprises at least one bond according to i), ii), iii), and iv).

14. The absorbent article according to claim 12, wherein the adhesive comprises a propylene-based polymer or a blend of propylene-based polymers.

15. The absorbent article according to claim 14, wherein the adhesive comprises at least 25% by weight of the propylene-based polymer or blend of propylene-based polymers.

16. The absorbent article according to claim 14, wherein at least one of the propylene-based polymer(s) has an enthalpy of fusion of at least 20 J/g, as measured by the Enthalpy of Fusion Measurement Method.

17. The absorbent article according to claim 1, wherein the absorbent article is a taped diaper comprising a liquid permeable topsheet, a liquid impermeable backsheet, an absorbent core having a core wrap disposed between the topsheet and the backsheet, an optional acquisition layer, and a landing zone;
   wherein the backsheet comprises a liquid impermeable film and a nonwoven outer cover, wherein the landing zone comprises a discrete nonwoven material which is bonded to the nonwoven outer cover;
   wherein the nonwoven-nonwoven adhesive bond is selected from one or more of:
   (i) a landing zone to backsheet bond;
   (ii) a topsheet to acquisition layer bond;
   (iii) an acquisition layer to core wrap bond;
   (iv) a topsheet to core wrap bond.

18. The absorbent article according to claim 17, wherein the nonwoven-nonwoven adhesive bond comprises at least a landing zone to backsheet bond.

19. The absorbent article according to claim 17, wherein the adhesive comprises a propylene-based polymer or a blend of propylene-based polymers.

20. The absorbent article according to claim 19, wherein the adhesive comprises at least 25% by weight of the propylene-based polymer or blend of propylene-based polymers.

* * * * *